Oct. 22, 1968 A. NILL Plant Pat. 2,841
AZALEA PLANT
Filed May 8, 1967
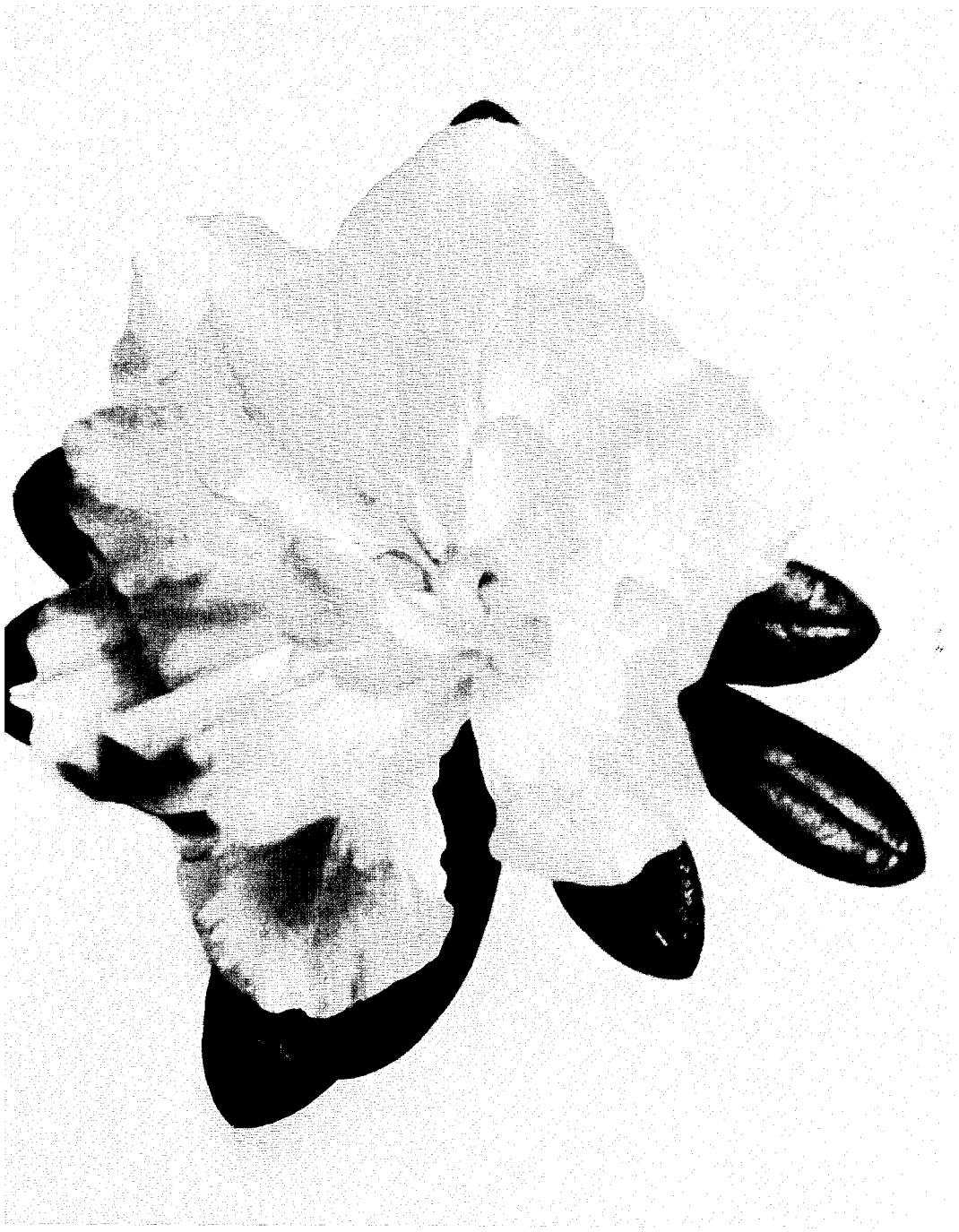
Inventor
Alfred Nill
By: Robb & Robb
Attorneys.

United States Patent Office

Plant Pat. 2,841
Patented Oct. 22, 1968

2,841
AZALEA PLANT

Alfred Nill, Wantagh, N.Y., assignor to Dauerheim, Inc., Wantagh, N.Y., a corporation of New York Filed May 8, 1967, Ser. No. 637,015
1 Claim. (Cl. Plt.—55)

The present invention relates to a new and distinct variety of azalea plant of the Indicum or Indian type, which was discovered by me in a greenhouse on the commercial nursery property of my assignee at Wantagh, Long Island, N.Y., as a sport of the azalea variety known as "Roberta" (Plant Patent No. 1,772).

At the time of my discovery aforesaid, plants of the variety "Roberta" were being commercially propagated and grown under my direction and supervision as foreman of said nursery. In the course of these operations, my attention was attracted to one plant amongst a block of plants of "Roberta" in one of the greenhouses, because of the unusual and distinctive color of the flowers on one shoot which differed from the typical flower color on the remainder of that plant and on all other plants of "Roberta" in that block. On closer examination of this particular plant, I found that it had sported, and I thereupon took immediate steps to preserve the sport and keep it under close observation. I also took steps in due course to asexually reproduce the sport, as performed under my direction and supervision at Wantagh, Long Island, N.Y., by both cuttings and grafting. Continued observations and tests of the sport and its progeny as derived by asexual reproduction thereof as aforesaid, convinced me that the new sport is a new and distinct variety which is substantially identical in all respects to the parent variety "Roberta," except for its flower color which is more red, with white varietgations, particularly on the tips of the outer petals and in the center of each flower, and the red coloring being clear and bright so that the flowers are very attractive and present a striking mass effect. This new flower color, taken together with the other outstanding features of the new sport which are otherwise similar to those of the parent variety "Roberta," represent a unique combination of characteristics which has great commercial value and distinguishes my new variety from all other azalea varieties of which I am aware, as evidenced by the following features, among others, which are particularly outstanding in the new variety:

(1) Vigorous and uniform habits of growth;

(2) Persistent and attractive dark green foliage;

(3) Firm texture and good keeping qualities of the flowers;

(4) A distinctive and attractive flower color corresponding to Jasper Red, near the edges of the petals, shading inwardly to La France Pink, with white areas at the tips of the outer petals and in the center of each flower, and with some yellow tints in the white areas of the flower centers; and (5) Excellent suitability for forcing.

The accompanying drawing shows a typical specimen flower and also portions of typical foliage specimens of the new variety as depicted in color as nearly true as it is reasonably possible to make the same in a color illustration of this character.

Being substantially identical in all respects to the parent variety "Roberta," except for its different flower color, the new sport may be considered as otherwise conforming to the detailed description embodied in my prior Plant Patent No. 1,772, issued Nov. 18, 1958, to which reference may be readily had, but for convenience, the following brief description of the new sport is given:

(Observations made from specimens grown in a greenhouse at Wantagh, Long Island, N.Y.)

Color designations are in accordance with Ridgway's Color Standards and Nomenclature, except where ordinary color terms have been employed.

Parentage: Sport of "Roberta."

Propagation: Holds its distinguishing characteristics through succeeding propagations by both cuttings and grafting.

Growth: Vigorous; similar in form and vigor to parent variety "Roberta."

Blooming habit: Same as "Roberta"; even; usually blooms from about February 1 to about April 15.

Foliage: Same as parent variety; persists.

*Size (mature).*—Length—from about 1¾ inches to 2 inches. Width—from about ½ inch to ⅝ inch.

*Shape.*—Fairly elliptical.

*Quantity.*—Normal.

*Texture.*—Same as in parent variety.

*Marging.*—Smooth.

*Color.*—Old foliage: upper side—Dark Dull Yellow-Green, Plate XXXII; under side—Chromium Green, Plate XXXII. New foliage: upper side—Spinach Green, Plate V; under side—Lettuce Green, Plate V.

Flowers:

*Borne.*—Usually 1 or 2 flowers per bud sheath.

*Quantity.*—Fairly free.

*Continuity.*—One crop per season.

*Size.*—Averages approximately 3 inches in diameter.

Petalage:

*Female flower.*—Similar to parent variety; hose-in-hose.

*Male flower.*—Similar to parent variety; hose-in-hose.

*Texture.*—Firm; harder than most indicum varieties.

*Color.*—Jasper Red, Plate XIII near edges of petals, shading inwardly to La France Pink, Plate I, with white areas at tips of petals (particularly the outer petals) and in center of each flower, and with white areas of flower centers having some yellow tints.

Bud:

*Form.*—Pointed.

*Color.*—Similar to open flowers.

Reproductive organs:

*Female flower.*—Styles—about 1½ inches long. Color—pink, with chartreuse stigma.

*Male flower.*—Few reproductive organs; stamens have one or more pink anthers with chartreuse pollen, but pollen does not detract from appearance of flower when flower is open, as stamens are shorter than styles and relatively insignificant; pollen holds color quite well.

I claim:

1. A new and distinct variety of azalea plant of the indicum type, substantially as herein shown and described, characterized particularly as to novelty by its general similarity to its parent variety "Roberta" (Plant Patent No. 1,772) in all respects except for its flower color, while differing therefrom by a distinctive and attractive variegated red-pink-white flower color corresponding to Jasper Red near the edges of the petals, shading inwardly to La France Pink, with white areas at the tips of the petals (particularly the outer petals) and in the center of each flower, and with some yellow tints in the white areas of the flower centers.

No references cited.

ROBERT E. BAGWILL, *Primary Examiner.*